(12) United States Patent
Logan

(10) Patent No.: US 6,887,217 B1
(45) Date of Patent: May 3, 2005

(54) HANDS-FREE BREAST PUMPING SYSTEM

(76) Inventor: Donna Logan, 1033 Northview St., Port Charlotte, FL (US) 33952

(*) Notice: Subject to any disclaimer, the term of this patent is extended or adjusted under 35 U.S.C. 154(b) by 201 days.

(21) Appl. No.: 10/340,226

(22) Filed: Jan. 10, 2003

(51) Int. Cl.$^7$ .............................................. A61M 1/06
(52) U.S. Cl. ..................................................... 604/74
(58) Field of Search ...................... 604/73–74, 118–119; 2/73, 69, 69.5, 104, 105, 106, 113, 114, 115; 450/36

(56) References Cited

U.S. PATENT DOCUMENTS

| | | | | |
|---|---|---|---|---|
| 949,414 A | * | 2/1910 | Cunningham | 604/76 |
| 2,440,466 A | * | 4/1948 | Freedman | 450/55 |
| 5,514,166 A | * | 5/1996 | Silver et al. | 604/74 |
| 6,004,186 A | * | 12/1999 | Penny | 450/36 |
| 6,213,840 B1 | * | 4/2001 | Han | 450/36 |
| 6,227,936 B1 | * | 5/2001 | Mendoza | 450/36 |
| 6,440,100 B1 | * | 8/2002 | Prentiss | 604/74 |
| 6,659,841 B2 | * | 12/2003 | Raimondo | 450/36 |

* cited by examiner

Primary Examiner—Manuel Mendez
(74) Attorney, Agent, or Firm—Frank A. Lukasik

(57) ABSTRACT

A device for expressing milk using a maternity brassier modified to accept a funnel shaped vacuum cup attached to a breast milk pump. An elastic/stretch bra is modified to include elasticized openings through which the shield can be deployed. The elasticized openings are expandable from one half inch to three inches.

4 Claims, 6 Drawing Sheets

HANDS-FREE BREAST PUMPING SYSTEM

BACKGROUND OF THE INVENTION

This invention relates generally to devices for expressing breast milk and more particularly to a maternity brassiere modified to accept a funnel shaped vacuum cup attached to a breast milk pump.

Breast pumps for extracting or expressing breast milk from a woman's breast for later use by an infant have been available for years. Typically, these breast pumps include a funnel shaped hood, or shield, that is placed over the nipple and a substantial portion of the breast. A reduced pressure or vacuum is intermittently generated in the hood in a manner which causes milk to be expressed from the breast within the hood. The milk then typically flows from the hood to a storage container for later use.

The process of expressing the breast milk as described, requires that the woman in some part, must disrobe or otherwise expose her breast(s) to the hood. In the event that she utilizes one of the prior art double hood breast milk pumps, then she almost certainly will remove her brassiere or undergarment in order to expose both breasts simultaneously. A process which is inconvenient and which requires privacy. Working or traveling mothers are disadvantaged by the need to express their breast milk wherein they must find a private place and manually manage the task throughout the process.

Prior art breast pumps, such as that disclosed in U.S. Pat. No. 5,797,875 issued Aug. 25$^{th}$ 1998 to Silver and U.S. Pat. No. 5,007,899 and the LACTINA breast pump assembly manufactured and sold by Medela, Inc. to which the latter patent relates, have in common, a funnel-shaped shield or hood which is integrally formed as an extension to a containment assembly for breast milk. The hood itself is not detachable.

Prior art brassieres such as those in U.S. Pat. No. 4,390,024 issued Jun. 28$^{th}$ 1983 to Williams, which discloses detachable flaps for exposing the breasts, and U.S. Pat. No. issued Apr. 18$^{th}$ 1899 to Murray, which discloses hinged breast flaps, do permit access to the nipples of the breasts but neither provide facility for retaining in position a breast shield attached to a breast pump. What is needed is a convenient system which allows a woman to discreetly manage breast pumping while also allowing her to operate the breast pump hands-free so she may simultaneously execute other tasks.

SUMMARY OF THE INVENTION

The present invention provides an improved breast pump shield or hood and an improved brassiere for holding the shield in place. In a preferred embodiment of the present invention, the shield portion of the shield is detachably fixed to the containment assembly and can be positioned and deployed by simply stretching the elastic of the brassiere to allow the cone to be placed over the breast and to be retained thereafter by the brassiere.

According to the first aspect of the invention, the improved breast pump assembly is mechanically compatible to prior art devices cited herein with the modification being made to the shield component to make it detachable for ease of deployment as will be disclosed in the drawing exemplars annexed hereto. According to the second aspect of the invention, a common elastic/stretch bra, sometimes described as a "sports" bra is modified to include elasticized openings through which the shield, can be deployed. The stretchable nature of the bra permits the deployment of the shield without the garment having to be removed, this along with the tendency of the bra to retain firm contact with the breast, facilitates convenient and private hands-free breast pumping. Once the shield is in place, it is easily connected to the pump and containment unit and will remain in place throughout the pumping process without having to be held there. It will be seen therefore that the present invention is a simple system improving not only the prior art breast pumps but also the prior art brassieres. In the case of the shield component, simply creating a separate piece of such dimensions as to be able to fit inside existing prior art shields as an adaptor, obviates the need to retool existing manufacturing and makes the unit a retrofitting for a variety of pumps from a variety of manufacturers. The unit, through retooling, also could be manufactured as an integral part of existing prior art breast pump units.

It is an object of the present invention to provide an elastic brassiere with facility for the deployment of a breast pump shield in privacy and without the user having to disrobe.

It is a further object of the invention to provide a system for breast pumping which is hands-free.

It is a further object of the invention to provide a shield component of a breast pump which is detachable for ease of deployment.

It is a further object of the invention to provide a shield of such dimension as to be adaptable as a retrofitting for existing breast pump systems.

It is a further object of the invention to provide prior art breast pump manufacturers with an improved design for, and as a possible alternative to, their existing breast pump units.

These and other features and advantages of the present invention will be further understood upon consideration of the following detailed description of the present invention, taken in conjunction with the accompanying drawings.

DETAILED DESCRIPTION OF A PREFERRED EMBODIMENT

Figure 1:
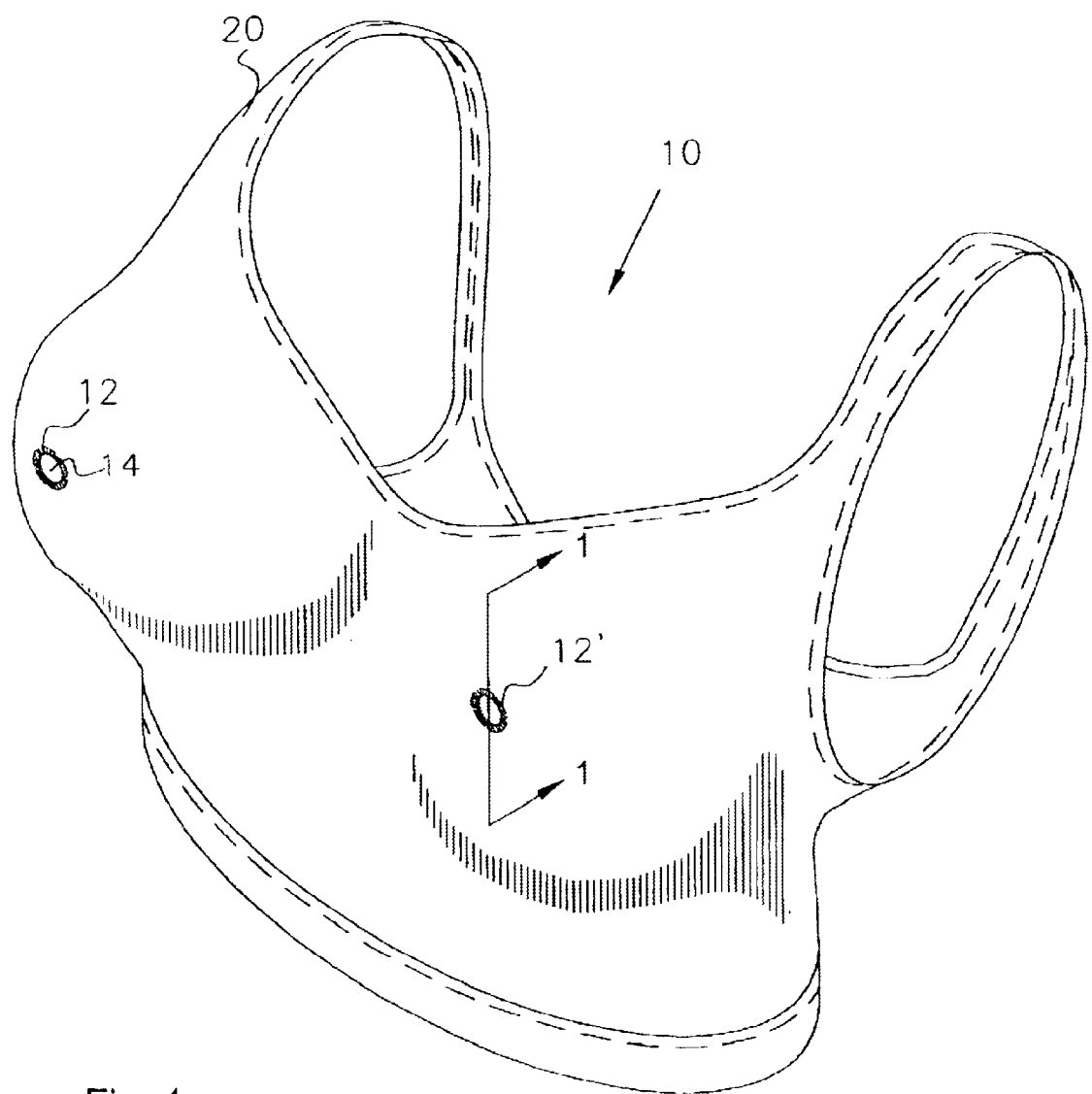
FIG. 1. is an isometric view of the invention brassiere showing a section line the view through which is shown in FIG. 2.
Figure 2:
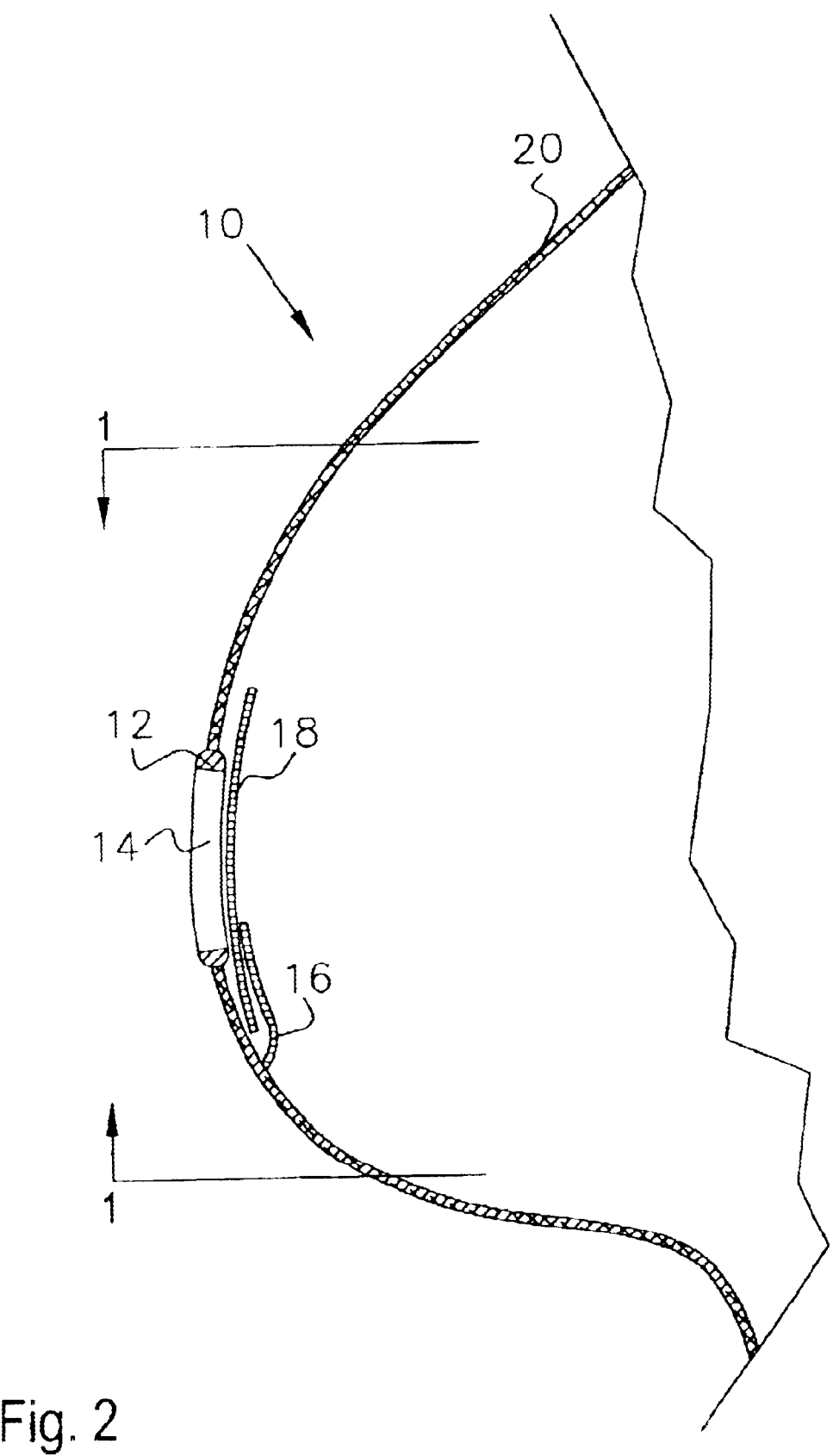
FIG. 2. is a sectional elevation of the invention brassiere showing its internal components and there relative positions, FIG. 3. is a sectional elevation of the invention brassiere through which the invention shield is deployed.

Referring to the drawings wherein like numerals refer to like and corresponding parts throughout the several views, in FIG. 1. the invention brassiere is designated overall by the numeral 10. Elasticized inserts, 12 and 12' define opening 14. Section lines A—A bisect insert 12' which is further illustrated in FIG. 2. to which reference is now made. Brassiere cup 20 generally comports with the shape of female breast and opening 14, (½"–3⅛") defined by elasticized insert 12 is generally positioned to correspond to the location of the nipple on a female breast. Detachable absorbent pad 18 is retained in position by pad retainer 16. Pad 18 being commonly available in prior art, is simple to position in order to provide an absorbent medium for seepage of breast milk and to provide an additional and optional means for containing the breast nipple within cup 20. Elastic insert 12 is shown in this view in a distended or expanded condition in order to fully disclose the existence of opening 14. In actual use, elastic insert 12 and 12' would be closed to reduce opening 14 to a size which would be almost non existent until expanded to accommodate shield 13 as shown in FIG. 3 to which reference is now made.

Figure 3:
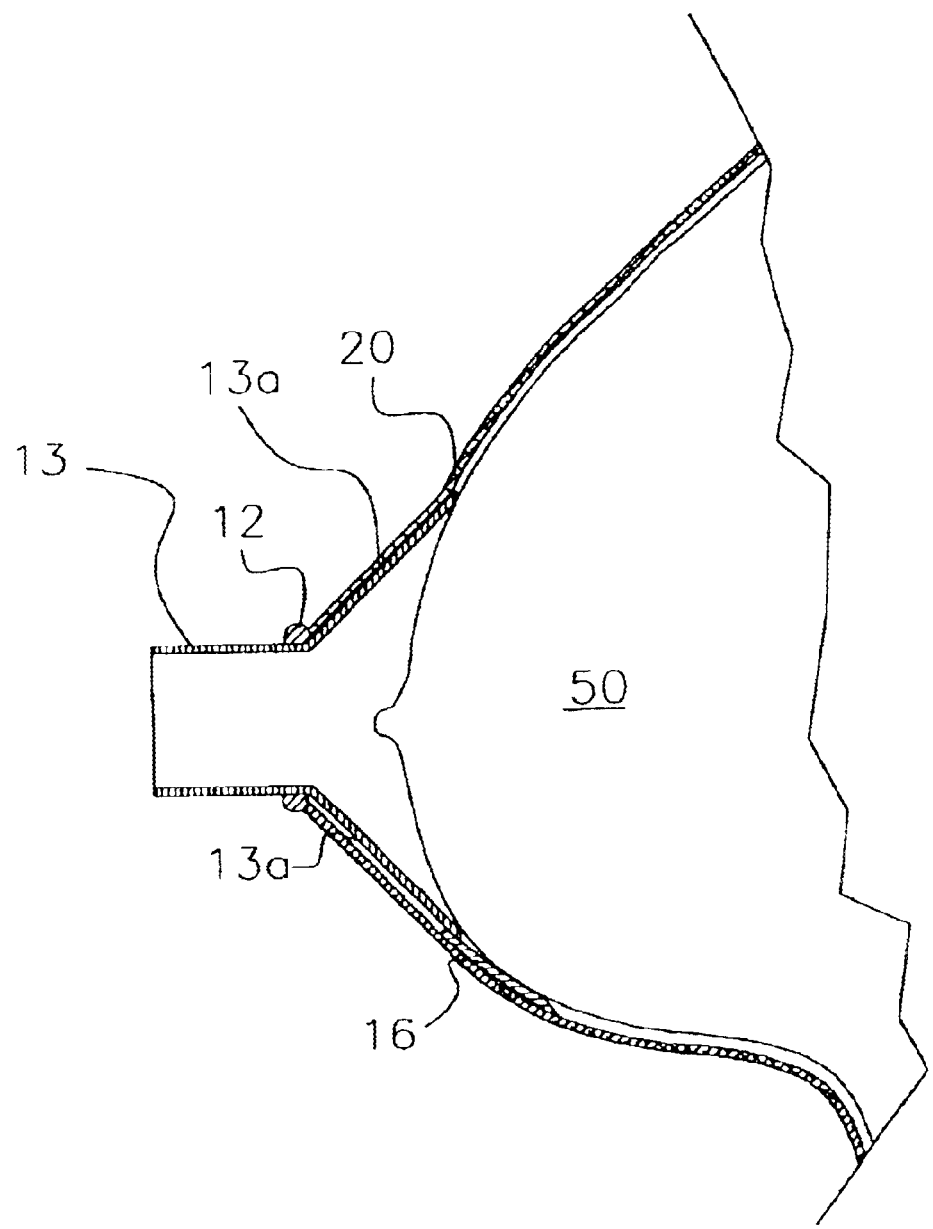

In FIG. 3 brassiere cup 20 retains breast 50. Shield 30 is positioned so as to surround the breast nipple and to form a seal against breast 50. Elastic bra cup 20 and insert 12 are distended to accommodate and to retain shield 13. Bra 20 presses against shield 13 on its conical surface 13a. Pad retainer 16 is depressed and displaced by shield 30 and does not interfere with the fitment or function of shield 13 or cup 20. Shield 30 being detachable, can be deployed by stretching cup 20 away from breast 50 and positioning shield 30 inside insert 13 (see FIG. 5).

Figure 4:
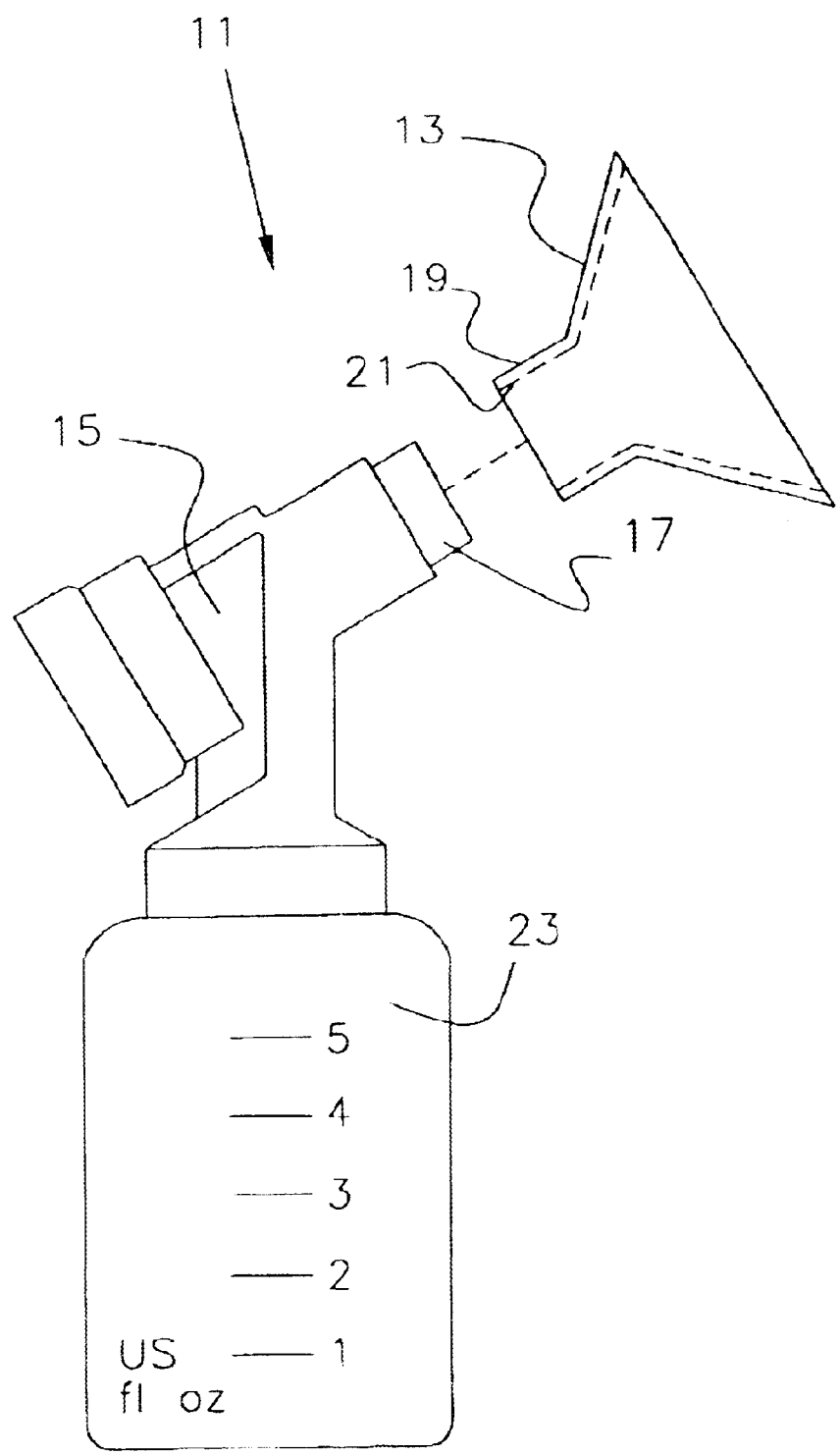
FIG. 4 is an elevational view partially in section of the invention shield showing its relative position to the breast milk containment unit.

Referring now to FIG. 4., and to the prior art exemplar of a breast milk pump containment unit, common elements between the invention pump 11 and the prior art are seen. The improved design of the present invention is seen in the detachable shield 13. Shield 13 can be constructed to fit tightly to the containment unit 15/23 over protrusion 17 which is inserted into opening 21. Alternately, outer diameter 19 of shield 13 can be sized so as to fit as an adaptor into the equivalent component of a prior art unit. The latter deployment would permit a woman to use her existing prior art unit as a pump, while being able to discreetly and conveniently deploy the present invention shield 13 as described and illustrated FIG. 5 to which reference is now made.

Figure 5:
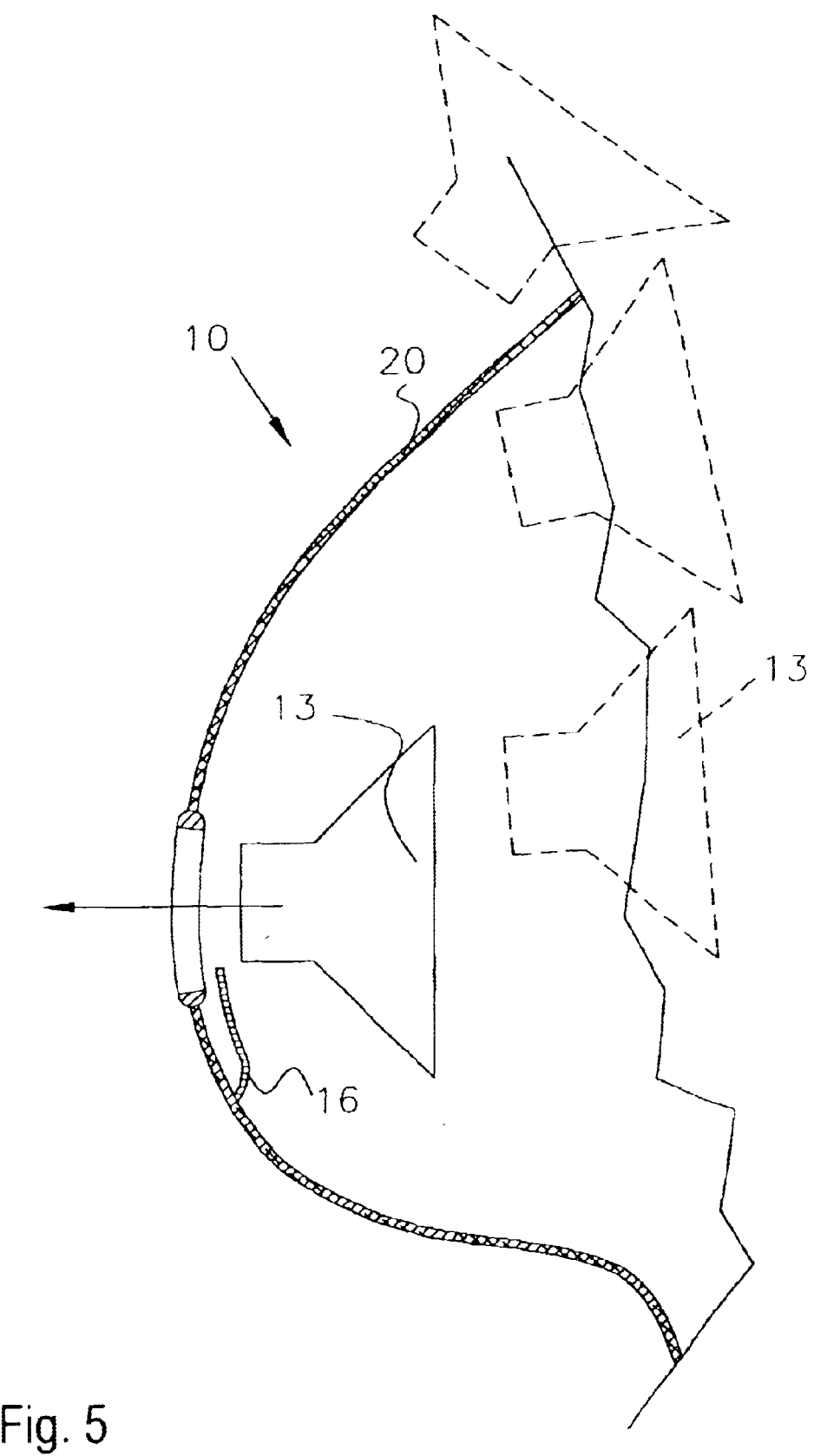
FIG. 5. is a sectional elevation of the invention brassiere and the invention shield as it is deployed.
Figure 6:
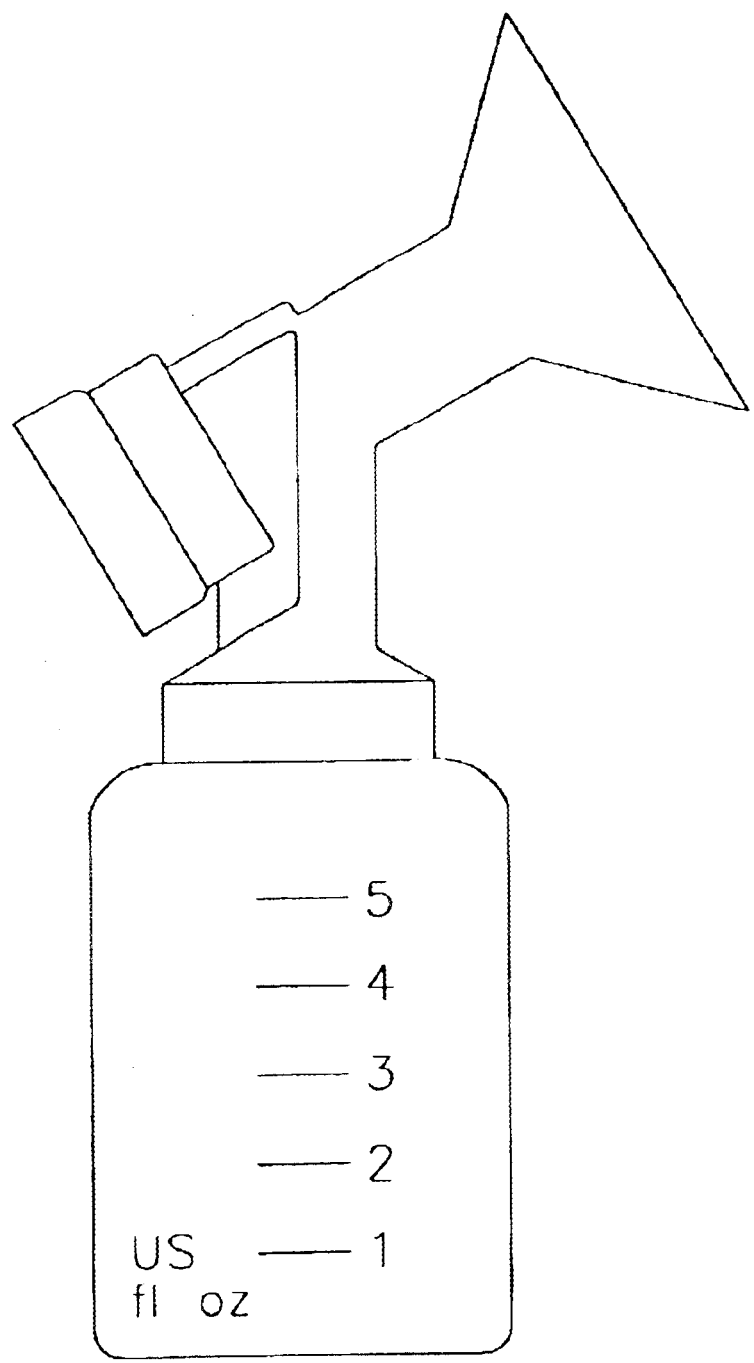
FIG. 6 A prior art exemplar of a breast pump containment unit is further annexed.

In FIG. 5 shield 13 deployed from the rear of cup 20 and does not require the user to try to stretch elastic insert 12 and 12' (FIG. 2,3) over the funnel end of shield 13.

What is claimed is:

1. A human breast milk pumping system comprising:
a common, elastic/stretch brassier, said brassier having a first elastic breast cup and a second elastic breast cup,
an elasticized circular insert being formed in each of said breast cups, said inserts being located generally central to said breast cups, said inserts being elastically expandable to form openings, said openings being expandable from a minimum of one half inch to three inches, and
a semicircular pad retainer being attached to the interior of each of said breast cups, said pad retainers being generally formed beneath each of said openings, said pockets providing a locating and retaining means for an absorbent pad.

2. A human breast milk pumping system comprising:
a common, elastic/stretch brassier, said brassier having a first elastic breast cup and a second elastic breast cup,
an elastic circular insert being formed in each of said breast cups, said inserts being located generally central to said breast cups, said inserts being elastically expandable to form openings, said openings being expandable from a minimum of one half inch to three inches, and
a semicircular pad retainer being attached to the interior of each of said breast cups, said pad retainers being generally formed beneath each of said openings, said pockets providing a locating and retaining means for an absorbent pad, and
a conical shield, said shield being generally funnel-shaped, said shield being of suitable size for fitment over the nipple area of a human breast, said shield being removably inserted into said openings in said cups, said openings retaining said shield in a position covering and concentric to the nipple of a human breast, said shield being attached to a breast milk pumping and containment device.

3. A human breast milk pumping system of claim 2 wherein said conical shield is removably attached to a breast milk pumping and containment device.

4. The conical shield of claim 2 further comprising a connecting means, said connecting means having proximal and distal ends, said proximal end being generally tubular, said proximal end being connected to said conical shield, said distal end being generally tubular, said distal end having a female thread, said thread forming a coupling means, said coupling being of equivalent dimension to the containment means of a human breast milk pump.

* * * * *